United States Patent [19]

Jensen et al.

[11] 4,322,271
[45] Mar. 30, 1982

[54] PROCESS FOR THE PREPARATION OF N-VINYL-N-ALKYL-CARBOXYLIC ACID AMIDES

[75] Inventors: Harald Jensen, Frankfurt am Main; Erwin Schmidt, Kelkheim; Michael Mitzlaff, Bad Homburg; Jürgen Cramer, Eppstein; Rudolf Pistorius, Ober-Mörlen; Hartmut Pietsch, Hofheim am Taunus; Klaus Dehmer, Kelkheim, all of Fed. Rep. of Germany

[73] Assignee: Hoechst Aktiengesellschaft, Frankfurt am Main, Fed. Rep. of Germany

[21] Appl. No.: 149,742

[22] Filed: May 14, 1980

[30] Foreign Application Priority Data

May 16, 1979 [DE] Fed. Rep. of Germany ....... 2919755

[51] Int. Cl.$^3$ ............................................ C07C 102/00
[52] U.S. Cl. .................................... 204/73 R; 564/215
[58] Field of Search ....................... 564/215; 204/73 R

[56] References Cited

U.S. PATENT DOCUMENTS

| | | | |
|---|---|---|---|
| 3,193,483 | 7/1965 | Balzer .................................... | 204/73 |
| 3,377,340 | 4/1968 | Hartwimmer et al. ....... | 260/239.3 R |
| 3,531,471 | 9/1970 | Hartwimmer et al. ............. | 252/437 |
| 3,534,099 | 10/1970 | Cookson et al. ..................... | 260/404 |
| 3,941,666 | 3/1976 | Mitzlaff et al. .................... | 204/73 R |
| 4,036,712 | 7/1977 | Mitzlaff ............................... | 204/59 R |
| 4,140,593 | 2/1979 | Mitzlaff ............................... | 204/59 R |
| 4,149,941 | 4/1979 | Mitzlaff et al. ................... | 204/59 R |

FOREIGN PATENT DOCUMENTS

| | | |
|---|---|---|
| 837906 | 7/1976 | Belgium . |
| 1235893 | 3/1967 | Fed. Rep. of Germany . |
| 1445237 | 3/1969 | Fed. Rep. of Germany . |
| 1545798 | 1/1970 | Fed. Rep. of Germany . |
| 2113338 | 9/1972 | Fed. Rep. of Germany . |
| 2336976 | 7/1973 | Fed. Rep. of Germany . |
| 2539767 | 3/1977 | Fed. Rep. of Germany . |
| 2081393 | 3/1971 | France . |
| 1125324 | 8/1968 | United Kingdom . |

OTHER PUBLICATIONS

Brehme, Synthesis, 1976, pp. 113–114.
Akerblom, Chem. Abst., 77, (1972), #48072.

*Primary Examiner*—Arthur P. Demers
*Attorney, Agent, or Firm*—Curtis, Morris & Safford

[57] ABSTRACT

N-Vinyl-N-alkyl-carboxylic acid amides are prepared, starting from N-ethyl-carboxylic acid amides, in a 3-stage process consisting of the following stages:

(a) anodic alkoxylation of the N-ethyl-carboxylic acid amides to give N-α-alkoxyethyl-carboxylic acid amides;

(b) alkylation of these N-α-alkoxyethyl-carboxylic acid amides with an alkyl halide or dialkyl sulfate in an alkaline medium to give N-α-alkoxyethyl-N-alkyl-carboxylic acid amides; and (c) splitting off of alcohol from the products of stage (b) by heating to temperatures between about 60° and about 350° C.

Instead of stages (b) and (c), it is also possible to carry out the following stages after stage (a):

(b$_1$) splitting off of alcohol from the N-α-alkoxyethyl-carboxylic acid amides obtained in stage (a) by heating to temperatures of about 60° to about 600° C., to give N-vinyl-carboxylic acid amides; and (c$_1$) alkylation of these N-vinyl-carboxylic acid amides by reaction with an alkylating agent of the same type as in stage (b) in an alkaline medium.

The N-vinyl-N-alkyl-carboxylic acid amides obtained by the process are valuable intermediate products, in particular for the manufacture of homopolymers and copolymers with interesting properties.

15 Claims, No Drawings

PROCESS FOR THE PREPARATION OF N-VINYL-N-ALKYL-CARBOXYLIC ACID AMIDES

N-Vinyl-N-alkyl-carboxylic acid amides are valuable intermediate products and are particularly suitable for the manufacture of homopolymers and copolymers with interesting and diverse technological properties.

A number of various methods are known for the preparation of N-vinyl-N-alkyl-carboxylic acid amides; these can essentially be divided into 2 groups, that is to say methods using secondary N-alkyl-carboxylic acid amides (N-alkyl-carboxylic acid amides which still carry an H atom on the N) and acetylene, that is to say $C_2H_2$, as starting materials, and methods in which alcohol is split off from N-α-alkoxyethyl-N-alkyl-carboxylic acid amides.

A. Methods using secondary N-alkyl-carboxylic acid amides and $C_2H_2$ as starting materials:

Certainly the first work in this direction originates with Reppe and co-workers; in Liebigs Ann. 601, 134 (1956), these authors described, inter alia, the preparation of N-vinyl-N-methylacetamide by reaction of N-methylacetamide with $C_2H_2$ with the addition of metallic potassium. However, after a reaction in an autoclave at 160°–180° C. for 48 hours, the yield was only 30% of theory.

The process was improved and further developed by varying the process conditions, being carried out sometimes in the liquid phase (German Patent Specification No. 1,176,124) and sometimes in the gas phase (German Patent Specification No. 1,196,657), but in these cases also, satisfactory degrees of reaction could not be achieved, although the yields of the desired N-vinyl-N-alkyl-carboxylic acid amides, relative to the starting material reacted, were relatively good (80–90%).

The main disadvantage of these processes based on acetylene, however, is the necessity for expensive safety measures because acetylene cannot be handled without danger.

B. Splitting off of alcohol from N-α-alkoxyethyl-N-alkyl-carboxylic acid amides:

According to the process of German Patent Specification No. 1,235,893, alcohol is split off from N-α-alkoxyethyl-N-alkyl-formamides in the presence of weakly acid, surface-active, insoluble substances or of mono-, di-, tri-, hydroxy- or keto-carboxylic acids which give the reaction mixture a pH value of between about 3 and 5.5, by heating to temperatures between 50° and 250° C., to give the corresponding N-vinyl-N-alkyl-formamides. In the preparation, for example, of N-vinyl-N-methyl-formamide from N-α-methoxyethyl-N-methyl-formamide by this process, a yield of 95%, relative to starting material reacted (conversion: 90.8%; see Example 1), is achieved.

To prepare the N-vinyl and N-alkenyl derivatives of acetamide and of the aliphatic acid amides next in the homologous series, the corresponding N-α-alkoxyalkyl-N-alkyl-carboxylic acid amides should be heated to about 50° to 180° to 200° C. in the presence of catalysts (U.S. Pat. No. 3,377,340 and British Patent Specification No. 1,125,324).

According to the process of the U.S. patent, this is said to take place in the liquid phase and in the presence of surface-active insoluble substances (aluminum oxide, aluminum phosphate or zirconium dioxide); the process of the British patent specification is carried out in the gas phase in the presence of weakly acid catalysts, some of which are identical to those mentioned in the U.S. patent. The catalysts recommended in the British patent specification are the weakly acid oxides of Al, Be, Zr or W, the weakly acid phosphates of Ca, Al, Mo, B or W and aluminosilicates in the H form (zeolites and the like). The catalysts can be applied to an inactive support, such as kieselguhr or active charcoal and the like.

The yields given, for example for the preparation of N-vinyl-N-methyl-acetamide, in the above mentioned patent and patent specification are between about 75 and 95% of theory, relative to starting material reacted.

A process which should likewise be mentioned in this group of methods is the process according to German Patent Specification No. 1,670,742, in which N-vinyl-N-alkyl-carboxylic acid amides are prepared by reacting N-alkyl-carboxylic acid amides which still carry an H atom on the amide nitrogen with acetaldehyde in the presence of strongly basic catalysts or acid catalysts which are non-volatile or have a low volatility, and by heating the resulting rection mixture to a temperature of 100°–350° C. in the presence of acid catalysts which are non-volatile or have a low volatility, for at most 60 seconds. The process thus does not entirely belong in the group of methods for the preparation of N-vinyl-N-alkyl-carboxylic acid amides by splitting off of alcohol from N-α-alkoxyethyl-N-alkyl-carboxylic acid amides, because no N-α-alkoxyethyl-N-alkyl-carboxylic acid amide is involved here. However, it can be supposed that an N-α-hydroxyethyl derivative analogous to the N-α-alkoxyethyl derivatives of N-alkyl-carboxylic acid amides is formed from the N-alkyl-carboxylic acid amide starting material which still carries an H atom on the amide nitrogen and acetaldehyde, and the vinyl compound is then likewise formed from the N-α-hydroxyethyl derivative by splitting off of water, in the same manner as the N-α-alkoxyethyl derivatives are formed by splitting off of alcohol. However, the success of the process depends greatly on maintaining the fairly critical reaction conditions; in addition, the yield and degree of conversion are not always completely satisfactory (see, for example, Example 1: preparation of N-vinyl-N-methyl-formamide from N-methyl-formamide and acetaldehyde, yield 80% for a degree of conversion of 49%).

The preparation of secondary N-vinyl-carboxylic acid amides, that is to say of amides which still carry 1 H atom on the amide nitrogen, is described, for example, in German Offenlegungsschrift No. 2,336,977. In this preparation, gaseous N-α-alkoxyethyl-carboxylic acid amides are heated to about 300°–600° C., the gas mixture thereby formed is condensed by cooling rapidly and the N-vinyl-carboxylic acid amide is isolated from the condensate. The process gives good yields, but is however limited to the preparation of secondary N-vinyl-carboxylic acid amides.

The starting materials for all the processes mentioned under group B (with the exception only of the process according to German Patent Specification No. 1,670,742) are N-α-alkoxyalkyl-N-alkyl-carboxylic acid amides and (in the case of the process according to German Offenlegungsschrift No. 2,336,977) N-α-alkoxyethyl-carboxylic acid amides. These are accessible in the following ways.

C. Preparation of the N-α-alkoxyalkyl-N-alkyl-carboxylic acid amides and N-α-alkoxyethyl-carboxylic acid amides:

N-α-Alkoxyalkyl-N-alkyl-carboxylic acid amides can be obtained, for example, by reaction of secondary N- alkyl-carboxylic acid amides and acetals or hemiacetals [Chem. Berichte 99, 2127 (1966); and German Patent Specification No. 1,273,533]. However, the yields of this process are not always satisfactory. Thus, for example, a yield of only 26% is given in Example 11 of German Patent Specification No. 1,273,533 (reaction of N-methylacetamide with acetaldehyde diethyl acetal to give N-α-ethoxyethyl-N-methylacetamide).

N-Alkyl- and N-dialkyl-carboxylic acid amides, inter alia, are alkoxylated with alcohols using certain conducting salts to give the N-α-alkoxyalkyl derivatives by an electrochemical process (German Offenlegungsschrift No. 2,113,338). However, the process is less suitable for the preparation of N-α-alkoxyethyl-N-alkyl-carboxylic acid amides (because if there are 2 alkyl groups on the amide nitrogen, alkoxylation does not generally take place selectively only on one alkyl group and the mixture formed is then difficult to separate), and is mainly suitable only for the preparation of secondary N-α-alkoxyalkyl-carboxylic acid amides which still have a H atom on the amide nitrogen.

The electrochemical preparation of secondary N-α-alkoxyethyl-carboxylic acid amides from N-α-carboxyethyl-carboxylic acid amides is described in German Offenlegungsschrift No. 2,336,976; however, the process first requires preparation of the N-α-carboxyethyl-carboxylic acid amides needed as starting materials, and this entails substantial effort.

The electrochemical process of anodic alkoxylation of secondary N-ethyl-carboxylic acid amides according to Belgian Patent Specification No. 837,906 is more specifically suitable for the preparation of secondary N-alkoxyethyl-carboxylic acid amides; the process is carried out with a certain minimum amount of current and with quite particular conducting salts.

Secondary N-alkoxyethyl-carboxylic acid amides are prepared in a particularly favorable manner by anodic alkoxylation of N-ethyl-carboxylic acid amides with an alcohol in an electrolysis cell with vitreous carbon as the anode material and at least one alkali metal alkosulfate and/or tetraalkylammonium alkosulfate as the conducting salt, according to U.S. application Ser. No. 149,149, filed May 14, 1980.

The N-α-alkoxyethyl-N-alkyl-carboxylic acid amides are thus accessible in practice only by a purely chemical route (secondary carboxylic acid amides+acetals or hemiacetals), in yields which are scarcely satisfactory. The route to the corresponding N-vinyl-N-alkyl-carboxylic acid amides via these compounds is thus hardly sufficiently economical.

On the other hand, the electrochemical processes mentioned, some of which proceed with excellent yields and are also very advantageous in other respects, are suitable in practice only for the preparation of secondary N-α-allkoxyethyl-carboxylic acid amides (which still have an amide hydrogen). However, subsequent N-alkylation of the chemically sensitive and sterically hindered N-α-alkoxyethyl-carboxylic acid amides and also of the corresponding N-vinyl-carboxylic acid amides has not yet been described, although N-alkylations of, for example, carboxylic acid anilides and of lactams with alkyl halides or with dimethyl sulfate in aqueous alkali metal hydroxide solution are known (see Synthesis 1976, 113-144, German Offenlegungsschrift No. 2,216,627, German Offenlegungsschrift No. 2,236,429, German Democratic Republic Patent Specification No. 117,446 and Belgian Patent Sepcification No. 802,829).

It was thus desirable and an aim to discover a route by which N-vinyl-N-alkyl-carboxylic acid amides can be prepared in a more economical manner than in the case of the known routes.

According to the invention, this object could be achieved in a satisfactory manner by the new 3-stage process described in more detail below.

The invention thus relates to a process for the preparation of N-vinyl-N-alkyl-carboxylic acid amides, chiefly those of the formula I

in which $R^1$=H, $CH_3$ or $C_2H_5$, preferably H or $CH_3$, and in particular $CH_3$, and $R^2$=$CH_3$ or $C_2H_5$, preferably $CH_3$, starting from N-ethyl-carboxylic acid amides of the formula II

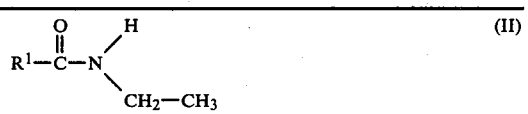

in which $R^1$ has the same meaning as in formula I, which comprises the following process steps:

(a) anodic alkoxylation of the N-ethyl-carboxylic acid amides of the formula II with alcohols of the formula III

in which $R^3$=($C_1$–$C_4$)-alkyl, preferably $CH_3$ or $C_2H_5$ and in particular $CH_3$, to give N-α-alkoxyethyl-carboxylic acid amides of the formula IV

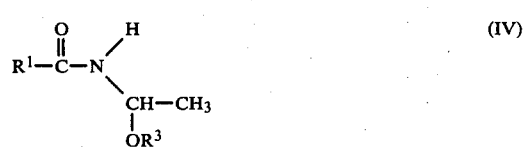

in which $R^1$ and $R^3$ have the same meaning as in the formulae I and III, (b) alkylation of the N-α-alkoxyethyl-carboxylic acid amide IV by reaction with an alkylating agent of the formula V

in which $R^2$ has the same meaning as in formula I and X=Cl, Br, I or $SO_4/2$, in an alkaline medium to give N-α-alkoxyethyl-N-carboxylic acid amides of the formula VI

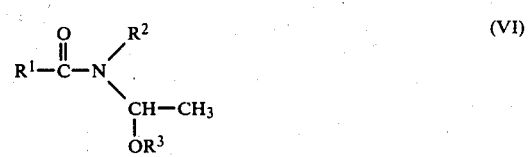

in which $R^1$, $R^2$ and $R^3$ have the meanings given for the above formulae, and (c) splitting off of the alcohol of the formula III from the N-α-alkoxyethyl-N-alkyl-carboxylic acid amides VI by heating to temperatures of about 60° to about 350° C., or, instead of stages b and c, after stage a (b₁) splitting off of the alcohol of the formula III from the N-α-alkoxyethyl-carboxylic acid amides IV by heating to temperatures of about 60° to about 600° C., to give N-vinyl-carboxylic acid amides of the formula VII

in which R¹ has the same meaning as in formula I, and (c₁) alkylating the N-vinyl-carboxylic acid amides VII by reaction with an alkylating agent of the formula V in an alkaline medium.

The process utilizes simple, readily accessible starting materials (N-ethyl-carboxylic acid amides II) and proceeds exceptionally smoothly and with high yields, these being over 90% of theory if the process is carried out carefully.

The combination of the 3 process steps i.e., (a) anodic alkoxylation+(b) alkylation+(c) splitting off of alcohol, or (a) anodic alkoxylation+(b₁) splitting off of alcohol+(c₁) alkylation, was not obvious at all. In spite of the need for an economical process for the preparation of N-vinyl-N-alkyl-carboxylic acid amides—and in spite of the three facts that (1) anodic alkoxylation of N-ethyl-carboxylic acid amides had been known for some time, (2) the alkylation of some N compounds was well known although it was not known to alkylate secondary N-α-alkoxyethyl- and N-vinyl-carboxylic acid amides such as are involved in the present invention) and (3) the splitting off of alcohol from N-α-alkoxyethyl-carboxylic acid amides had also been known for a number of years—the 3 process steps in question had not prior to the present invention yet been combined to provide a total uniform and economical process. It was also not obvious to apply the methods which are in themselves known for the alkylation of N compounds and in particular of some carboxylic acid anilides and lactams in an alkaline medium to secondary N-α-alkoxyethyl- and N-vinyl-carboxylic acid amides, because these particular secondary carboxylic acid amides are considerably more unstable in an alkaline medium than, for example, carboxylic acid anilides and lactams and also, for example, N-α-alkoxyethyl-N-alkyl- and N-vinyl-N-alkyl-carboxylic acid amides.

Starting substances for the 3-stage process according to the invention are N-ethyl-carboxylic acid amides of the above formula II (N-ethyl-formamide, -acetamide and -propionamide); preferred starting materials are N-ethyl-formamide and -acetamide, and N-ethyl-acetamide is particularly preferred. These compounds are readily accessible in a known manner, for example from the free carboxylic acids or esters thereof and ethylamine.

(a) In the first process stage, that is to say anodic alkoxylation, the starting N-ethyl-carboxylic acid amides II are electrolyzed with alcohols of the formula III [(C₁-C₄)-alkanols, preferably methanol or ethanol and in particular methanol]. This is advantageously effected by the processes of German Offenlegungsschrift No. 2,113,338 or Belgian Patent Specification No. 837,906.

Anodic alkoxylation by the process of U.S. application Ser. No. 149,149, filed May 14, 1980, filed at the same time, in an electrolysis cell with an anode of vitreous carbon and at least one alkali metal alkosulfate and/or tetraalkylammonium alkosulfate as the conducting salt is particularly advantageous; preferred conducting salts are Na methosulfate and ethosulfate, K methosulfate and ethosulfate and tetramethylammonium methosulfate and ethosulfate, and tetramethylammonium methosulfate is particularly preferred.

Cathode materials which can be used are the base metals customary for this purpose, such as steel, nickel and the like. It is possible to use either a single conducting salt or a mixture of conducting salts.

The starting solution for the electrolysis contains the N-ethylcarboxylic acid amide starting material and the conducting salt in alcoholic solution. The molar ratio of N-ethyl-carboxylic acid amide to alcohol is advantageously between about 1:1 and about 1:100, preferably between about 1:2 and about 1:60 and in particular between about 1:5 and about 1:50.

It is expedient for the concentration of the conducting salt in the (total) electrolysis solution to be at least about 0.1% by weight, preferably between about 5 and about 20% by weight.

The conducting salt is in most cases added after the alcoholic solution has been prepared, but the sequence can also be changed.

Water does not have to be excluded completely from the electrolysis, since small amounts of moisture hardly affect the course of the reaction. The amount of current advantageously used in the electrolysis process according to the said patent application filed at the same time is at least about 2.5 faradays/mole of starting compound. Smaller amounts of current are possible, but they reduce the conversion of the carboxylic acid amides II.

The current density is appropriately adjusted to between about 10 and 1,000 mA/cm², preferably between about 20 and 600 mA/cm². Lower current densities are possible, but afford no advantage; rather, they retard the formation of the product.

A temperature which is below the boiling point of the particular alcohol and above the melting point of the electrolysis solution is advantageously chosen as the temperature at which the electrolysis is carried out. In general, temperatures of about −10° to +100° C., preferably of about 0° to 60° C., are used.

The electrolysis is usually carried out under atmospheric pressure, but it is also possible, although of no advantage, to carry it out under reduced or increased pressure.

It is advantageous to carry out the electrolysis in the presence of an inert gas, such as, for example, nitrogen, in order to avoid explosive gas mixtures of hydrogen (formed during the electrolysis) and air.

The process can be carried out either continuously or discontinuously. It is distinguished by the particular advantage that, in contrast to the known erosion of material, even in the case of electrodes of vitreous carbon (see N. L. Weinberg "Technique of Electroorganic Synthesis", volume 5, part I, page 19, paragraph 2; John Wiley Verlag 1972), virtually no erosion occurs in the electrolyte system used in this process. Furthermore, no troublesome sparingly soluble precipitate forms on the cathode, this being frequently observed when F-containing conducting salts are used.

Finally, because of the relatively high solubility in alcohols of the conducting salts (alkosulfates) used in this electrolysis process, it is also possible to use considerably higher current densities than in the known processes of the state of the art, which are chiefly carried out in tetrafluoborates, hexafluophosphates and nitrates which are less soluble in alcohols; higher conversions are thereby possible in a shorter time.

(b) Alkylation of the N-α-alkoxyethyl-carboxylic acid amides IV obtained in stage (a):

All the possible agents for N-alkylation of carboxylic acid amides can be used as the alkylating agents, but alkylating agents which have proved most appropriate are those of the formula

$$R^2X \qquad (V)$$

in which $R^2$ denotes the methyl or ethyl group, preferably the methyl group, and X is Cl, Br, I or half an equivalent of a sulfate group. Examples of alkylating agents are: methyl chloride, methyl bromide, methyl iodide, dimethyl sulfate, ethyl chloride, ethyl iodide and the like; methyl chloride is the preferred alkylating agent.

The alkylating agent is appropriately employed in an amount from about the equimolar amount up to an approximately 100 (mole) % excess, relative to the N-α-alkoxyethyl-carboxylic acid amide IV to be alkylated. A larger excess retards the alkylation and leads to losses of alkylating agent and alkali by saponification. If less than the equimolar amount of alkylating agent is used, N-α-alkoxyethyl-carboxylic acid amide IV is lost as a result of side reactions.

The process should furthermore appropriately be carried out such that an excess both of alkylating agent and of alkali is always present relative to the N-α-alkoxyethylcarboxylic acid amide IV. It is indeed possible for the overall ratio of alkylating agent to amide IV to be not greater than an equimolar ratio; in this case the process would have to be carried out by metering the amide IV and alkali into the initially introduced alkylating agent.

The alkaline medium during the alkylation reaction is advantageously produced by introduction of an alkali metal hydroxide, in particular NaOH and/or KOH. NaOH is particularly preferred.

The alkali metal hydroxide can be employed in the commercially available forms, for instance as a powder or as lozenges, flakes and the like, or also as an approximately 50% strength aqueous solution. The amount of alkali metal hydroxide is such that the concentration of alkali metal hydroxide at the end of the reaction is still at least 20%, since otherwise scarcely any further alkylation takes place. If solid alkali metal hydroxide is used, an approximately 40-60% excess is appropriate. If the excess of alkali is lower, non-alkylated starting amide IV remains to an increasing extent. If the alkylation is carried out with solid alkali metal hydroxide and/or with the addition of solvents, the reaction is significantly accelerated by adding phase transfer catalysts. Examples of phase transfer catalysts which are suitable are quaternary ammonium and phosphonium salts and sulfonium salts, such as, for example, benzyl-triethyl-ammonium chloride, tetrabutylammonium sulfate, tetramethylphosphonium bromide and the like. The quaternary ammonium salts are preferred, and tetramethyl- and tetraethyl-ammonium chloride and sulfate are particularly preferred, these compounds also additionally having the advantage, as have ammonium salts in general, of catalyzing the subsequent splitting off of alcohol at low temperatures (about 60° to 70° C.). In this case, the alkylation reaction (b) and splitting off of alcohol (c) can therefore in principle be combined in one reaction vessel.

If solid alkali metal hydroxide is used, it is appropriate to suspend it in a diluent before the start of the reaction, the alkylation end product itself being a particularly suitable diluent. Other diluents are, for example, methylene chloride, toluene, xylene and the like, which are also suitable for washing out the reaction vessel and rinsing the filter cake.

The alkylation is appropriately carried out in the temperature range between about +10° and about +60° C., but the reaction is not restricted to this temperature range. Below about 10° C., the alkali metal hydroxide solution employed or the alkaline medium becomes increasingly more viscous and the reaction proceeds increasingly more slowly. Above about +60° C., the yield of alkylation product slowly starts to fall and an increasing amount of alkylating agent is consumed as a result of side reactions.

In order to bring the alkylation to completion in about 3 to 6 hours, it is advantageously carried out in approximately 50% strength aqueous sodium hydroxide solution at about 20° to about 40° C., or at about 30°–60° C. if solid alkali metal hydroxide is used.

The alkylation mixture is worked up in the customary manner. For example, if aqueous sodium hydroxide solution is used, the organic phase is separated off by decanting or centrifuging. If solid alkali is used, the reaction product can be isolated by filtration. The inorganic residues can be extracted with organic solvents (for example toluene). The reaction product is then distilled under normal pressure or, advantageously, reduced pressure, if appropriate after stripping off the solvent.

(c) Splitting off of the alcohol III from the N-α-alkoxyethyl-N-alkyl-carboxylic acid amides VI obtained in stage (b):

The alcohol is split off from the products VI, without or with catalysts, in the temperature range from about 60° to about 350° C., preferably from about 180° to 350° C. In the lower part of this temperature range, the reaction can be carried out in the liquid phase, whilst only a gas phase reaction is possible in practice at the higher temperature. Catalysts which can be used are virtually all the substances known for splitting off of alcohol from N-α-alkoxyalkyl-N-alkyl-carboxylic acid amides to give the corresponding vinyl compounds, such as, for example, the weakly acid oxides of Al, Be, Zr and W, the weakly acid phosphates of Ca, Al, Mo, B and W, or aluminosilicates in the H form (zeolites and the like), if appropriate on supports such as kieselguhr, active charcoal and the like (U.S. Pat. No. 3,377,340 and British Patent Specification No. 1,125,324). Ammonium salts, above all ($C_1$–$C_4$)-alkylammonium halides, sulfates and phosphates, are also favorable catalysts.

The other conditions of the splitting reaction (reduced pressure, normal pressure and the like) and the apparatus are also suitably those known in the art.

Instead of the reaction stage sequence of anodic alkoxylation a - alkylation b - splitting off of alcohol c, the anodic alkoxylation a can also be followed by the splitting off of alcohol $b_1$ from the N-α-alkoxyethylcarboxylic acid amides IV to give the N-vinyl-carboxylic acid amides VII and alkylation $c_1$ thereof to give the desired end products. The step sequence a-b-c is, nevertheless, peferable to the sequence a-$b_1$-$c_1$.

The splitting off of alcohol $b_1$ from the compounds IV is carried out analogously to the splitting off of alcohol from the corresponding N-α-alkoxyethyl-N-alkylcarboxylic acid amides VI in stage c. The preferred temperature range for this splitting is, however, higher than in the case of stage c, and in particular is about 180° to 600° C. The same conditions as for the alkylation of the N-α-alkoxyethyl-carboxylic acid amides IV in stage b likewise apply to the alkylation of the N-vinyl-carboxylic acid amides VII according to stage $c_1$.

All the stages of the combination process according to the invention proceed in a simple manner and with excellent yields, so that the total yields of the process are also as a rule above 90% of theory, relative to the starting N-ethyl-carboxylic acid amides II, and in particular independently of whether the process is carried out by reaction sequence a-b-c or a-$b_1$-$c_1$. The process thus represents a considerable technical and economic advance in the field of the preparation of N-vinyl-N-alkyl-carboxylic acid amides, in particular of N-vinyl-N-methyl-acetamide.

The invention will now be illustrated in more detail with the aid of the following examples.

(a) Anodic Alkoxylation

Only examples of the embodiment of the anodic alkoxylation according to the U.S. application Ser. No. 149,149, filed May 14, 1980, which is preferred for the process according to the invention are given here, since anodic alkoxylation is otherwise performed according to the state of the art (German Offenlegungsschrift No. 2,113,338, Belgian Patent Specification No. 837,906 and the like).

EXAMPLES 1–7

A mixture of the particular carboxylic acid amide and the appropriate alcohol in which the conducting salt is dissolved is introduced into an electrolysis cell, according to the FIGURE of German Offenlegungsschrift No. 2,113,338, with a capacity of about 500 ml and with a lid and reflux condenser. One plate each of steel and vitreous carbon (width×length=50×130 $mm^2$) are arranged in the cell such that they are 3 to 5 mm apart and are immersed in the solution to a depth of 100 mm. During the electrolysis, the contents of the cell are stirred at 50 to 60 revolutions per minute with the aid of a magnetic stirrer and the temperature T is kept at the value indicated in each case in the following Table 1. After the amount of current Q (also given in Table 1) has been passed through, the current is switched off.

The electrolysis solution is worked up in a known manner.

The results of Examples 1 to 7 are summarized in the following Table 1:

TABLE 1

| Example No. | Amide $R^1CONHC_2H_5$ R¹ | [g] | Alcohol R'OH R' | [g] | Conducting salt | [g] | Electrolysis data J | $\bar{U}$ | Q | T | Product | Yield M | S |
|---|---|---|---|---|---|---|---|---|---|---|---|---|---|
| 1 | H | 100 | $CH_3$ | 250 | Tetramethyl-ammonium methosulfate | 50 | 50 | 12.3 | 3.0 | 45 | N-(α-Methoxy-ethyl)-formamide | 74.1 | 49.4 |
| 2 | H | 100 | $CH_3$ | 250 | Sodium methosulfate | 15 | 45 | 29.9 | 3.8 | 20 | N-(α-Methoxy-ethyl)-formamide | 72.0 | 37.9 |
| 3 | H | 100 | $CH_3$ | 250 | Potassium methosulfate | 9 | 45 | 50.1 | 3.1 | 10 | N-(α-Methoxy-ethyl)-formamide | 70.9 | 45.7 |
| 4 | $CH_3$ | 100 | $C_2H_5$ | 263 | Tetramethyl-ammonium methosulfate | 50 | 30 | 47.3 | 4.2 | 10 | N-(α-Ethoxy-ethyl)-acetamide | 52.1 | 24.8 |
| 5 | $CH_3$ | 100 | $C_2H_5$ | 263 | Tetra-ethyl-ammonium ethosulfate | 60 | 30 | 29.2 | 4.8 | 30 | N-(α-Ethoxy-ethyl)-acetamide | 51.3 | 21.4 |
| 6 | $CH_3$ | 90 | n-$C_4H_9$ | 300 | Tetra-methyl-ammonium methosulfate | 30 | 20 | 49.2 | 4.8 | 30 | N-(α-n-Butoxy-ethyl)-acetamide | 45.1 | 18.8 |
| 7 | $C_2H_5$ | 60 | $CH_3$ | 300 | Tetra-methyl-ammonium methosulfate | 45 | 20 | 19.9 | 4.0 | 20 | N-(α-Methoxy-ethyl)-propionamide | 80.3 | 40.2 |

J = Current density [mA/$cm^2$]
$\bar{U}$ = Average cell voltage [V]
Q = Amount of current [faradays/mole of amide]
T = Cell temperature [°C]
M = Material yield [% of theory]
S = Current efficiency [%]

EXAMPLES 8–10

An undivided electrolysis cell with a block-like combination of electrodes is incorporated into a flow-through apparatus with a circulatory pump, heat exchanger and degassing vessel. This combination of electrodes consists of an anode of vitreous carbon and a steel cathode and, connected in a bipolar manner in between, four electrode plates of vitreous carbon. A stack of nickel fabric (2 layers of mesh width 0.19 mm and wire thickness 0.1 mm, and in between two layers of mesh width 0.5 mm and wire thickness 0.3 mm) and of polyethylene fabric (1 layer of mesh width 0.9 mm and filament thickness 0.3 mm) is inserted between each of these plates such that the nickel fabric comes to rest on the cathode sides of the carbon plates and on the steel plate. On incorporation, this combination is pressed together to minimize the distance between the electrodes. All these electrode plates are in a polyethylene frame which, at right angles to the direction of flow of the electrolyte was 22 mm wide, and parallel to the direction of flow was 12 mm wide, and like each of the plates was about 2.5 mm thick. The effective electrode surface of each anode was 255 cm².

The examples carried out in this apparatus are summarized in the following Table 2:

TABLE 2

| Example No. | Amide CH$_3$CONHC$_2$H$_5$ [g] | R'OH R' | [g] | Conducting salt | [g] | Electrolysis data J | U | Q | T | Product | Yield M | S |
|---|---|---|---|---|---|---|---|---|---|---|---|---|
| 8 | " | 4,830 CH$_3$ | 6,485 | Tetramethylammonium methosulfate | 2,485 | 157 | 30.1 | 2.8 | 48 | N-(α-Methoxyethyl)-acetamide | 86.5 | 61.8 |
| 9 | " | 2,000 " | 10,000 | Tetramethylammonium methosulfate | 3,000 | 179 | 25.8 | 3.0 | 37 | N-(α-Methoxyethyl)-acetamide | 89.3 | 59.5 |
| 10 | " | 6,000 " | 1,000 | Tetramethylammonium methosulfate | 3,750 | 153 | 26.3 | 2.6 | 46 | N-(α-Methoxyethyl)-acetamide | 91.9 | 70.7 |

For the explanation of the symbols, compare Table 1

(b) Alkylation

EXAMPLE 1

N-α-Methoxyethyl-N-methyl-formamide 20.6 g (0.2 mole) of N-α-methoxyethyl-formamide are added dropwise to a mixture, cooled to 5°–10° C., of 160 g of 50% strength sodium hydroxide solution and 31.5 g (0.25 mole) of dimethyl sulfate in the course of 30 minutes, while stirring intensively. The mixture is subsequently stirred at the same temperature for 30 minutes, excess dimethyl sulfate is decomposed by adding aqueous ammonia, the mixture is extracted with i-propyl ether and, after stripping off the solvent, the residue is distilled in vacuo. 21.3 g (91% of theory) of N-α-methoxyethyl-N-methyl-formamide of boiling point$_{17}$ 80°–83° C. are obtained.

EXAMPLE 2

N-α-Ethoxyethyl-N-methyl-acetamide 37.8 g (0.3 mole) of dimethyl sulfate and 26.2 g (0.2 mole) of N-α-ethoxyethyl-acetamide are simultaneously added dropwise to 100 ml of 50% strength sodium hydroxide solution at 10°–15° C., while stirring intensively. The mixture is subsequently stirred for 3 hours, residual dimethyl sulfate is decomposed by adding concentrated ammonia, the phases are separated in a separating funnel, the aqueous layer is extracted several times with toluene and, after stripping off the solvent, the residue is distilled in vacuo. 26.1 g (90% of theory) of N-α-ethoxyethyl-N-methylacetamide of boiling point$_{24}$ 90°–94° C. are obtained.

EXAMPLE 3

N-α-Methoxyethyl-N-ethyl-acetamide 136 (1.25 moles) of methyl bromide are added dropwise to a mixture of 117 g (1 mole) of N-α-methoxyethyl-acetamide, 500 ml of anhydrous dimethylsulfoxide and 70 g (1.25 moles) of powdered potassium hydroxide at 25° C., while stirring. 2 hours after the dropwise addition has ended, the mixture is extracted thoroughly with hexane. After stripping off the solvent, the reaction product is fractionated in vacuo. 50 g (34.5% of theory) of N-α-methoxyethyl-N-ethyl-acetamide of boiling point$_{16}$ 83°–85° C. are obtained.

$^1$H-NMR (CDCl$_3$): 1.0–1.45 (m); 2.1 (s) 3.1–3.45 (m); 4.8–5.1 (q); and 5.65–6.0 (q) ppm.

EXAMPLE 4

N-α-Methoxyethyl-N-ethyl-acetamide 58.5 g (0.5 mole) of N-α-methoxyethyl-acetamide and 84.2 g (0.55 mole) of ethyl iodide are simultaneously added dropwise to 300 ml of 50% strength sodium hydroxide solution at 10° C. Two hours after the addition has ended, the phases are separated in a separating funnel, the aqueous portion is extracted with hexane and, after stripping off the solvent, the residue is distilled in vacuo. 37 g (51% of theory) of N-α-methoxyethyl-N-etyl-acetamide of boiling point$_{16}$ 83°–85° C. are obtained.

$^1$H-NMR (CDCl$_3$): 1.0–1.45 (m); 2.1 (s); 3.1–3.45 (m); 4.8–5.1 (q); and 5.65–6.0 (q) ppm.

EXAMPLE 5

N-α-Methoxyethyl-N-methyl-acetamide 25 g (0.2 mole) of dimethyl sulfate are added to 500 ml of 50% strength sodium hydroxide solution at 5°–10° C., and 158 g (1.25 moles) of dimethyl sulfate and 117 g (1.0 mole) of N-α-methoxyethyl-acetamide are simultaneously added dropwise in the course of 3 hours, while stirring. After a further 3 hours, 50 ml of concentrated ammonia are added, and after 30 minutes, the phases are separated in a separating funnel and the aqueous layer is extracted with diethyl ether. After stripping off the solvent, distillation of the residue in vacuo gives 120 g (92% of theory) of N-α-methoxyethyl-N-methyl-acetamide of boiling point$_{18}$ 76°–81° C.

$^1$H-NMR (CDCl$_3$): 1.2 (d); 1.35 (d); 1.05 (d); 1.25 (d); 3.15 (d); 4.85–5.15 (q); and 5.6–5.9 (q) ppm.

EXAMPLE 6

N-α-Methoxyethyl-N-methyl-acetamide 1,800 g of 50% strength sodium hydroxide solution, 900 g of sodium hydroxide in the form of flakes and 300 g of methyl chloride are initially introduced into a pressure kettle provided with an anchor stirrer. 1,760 g of N-α-methoxyethyl-acetamide and 1,000 g of methyl chloride are uniformly metered in over a period of 3 hours. After a further 3 hours, the kettle is depressurized and the contents are degassed by passing in nitrogen. The reaction product with a lower specific gravity is separated from the inorganic constituents with a higher specific gravity in a centrifuge, and the reaction product is decanted off and distilled in vacuo. 1,804 g (91% of theory) of N-α-methoxyethyl-N-methylacetamide of boiling point$_{1.0}$ 48° are obtained.

The following yields are produced by varying the reaction temperature and under otherwise identical conditions:

| Reaction temperature (°C.) | Yield (%) | Starting material recovered |
| --- | --- | --- |
| 10 | 50 | 40 |
| 15 | 81 | 7,5 |
| 20 | 92 | 2,5 |
| 25 | 83 | — |
| 30 | 83 | — |
| 40 | 81 | — |
| 50 | 70 | — |

EXAMPLE 7

N-α-Methoxyethyl-N-methyl-acetamide 525 g of N-α-methoxyethyl-N-methyl-acetamide, as the diluent, 700 g (17.5 moles) of sodium hydroxide in the form of flakes, 30 g of water and 100 g (2 moles) of methyl chloride are initially introduced, at 40°, into a pressure kettle provided with an anchor stirrer. 1,170 g (10 moles) of N-α-methoxyethyl-acetamide and 525 g (10.5 moles) of methyl chloride are simultaneously delivered into the kettle in the course of 3 hours, while cooling with water. When the delivery has ended, the mixture is stirred at 40° for 3 hours. The contents of the kettle are discharged through a polyester filter. The kettle and filter cake are rinsed with methylene chloride. After stripping off the solvent from the filtrate, distillation of the residue in vacuo gives 1,717 g of N-α-methoxyethyl-N-methyl-acetamide (91% of theory, after subtracting the product employed as the diluent) of boiling point$_{1.5}$ 49°–51°, and 33 g (3% of theory) of non-methylated starting material.

If the reaction is carried out under identical experimental conditions with the exception of reaction temperature, which is indicated below, the following yields are obtained.

| Reaction temperature (°C.) | 20 | 30 | 40 | 50 | 60 |
| --- | --- | --- | --- | --- | --- |
| Yield of end product (%) | 74 | 83 | 90 | 92 | 73 |
| Starting material recovered (%) | 9 | 7 | 3 | 3 | 6 |

EXAMPLE 8

α-Methoxyethyl-N-methyl-acetamide

The procedure of Example 7 is followed at 20°, with the exception that, under otherwise identical reaction conditions, 50 g of a $C_{12}/C_{18}$-alkyl-dimethylbenzylammonium chloride, 50% strength in water, are added, instead of 30 g of water, to the mixture of sodium hydroxide and N-α-methoxyethyl-N-methylacetamide before the remaining reactants are metered in. Even at 20°, N-α-methoxyethyl-α-N-methylacetamide is obtained in a yield of 92%.

For rectification, the crude product is distilled with a thin film evaporator in a continuous column under 1 mm Hg. N-α-Methoxyethyl-N-methyl-acetamide (yield: 92%) is taken off at the top of the column and nonmethylated starting material (5%) is removed at the bottom of the column.

(c) Splitting off of alcohol

EXAMPLE 1

N-α-Methoxyethyl-N-methylacetamide is vaporized in a thin film evaporator at 270° under a blanket of nitrogen. The vapor is passed through an oven, filled with a porous silicic acid as a catalyst. The products of the splitting are condensed at the end of the oven. Table 1 shows the content, in the condensate, of starting material as a function of the oven temperature for a throughput of 400 g of starting material/hour.

| Temperature (°C.) | N-α-Methoxyethyl-N-methyl-acetamide, residual content (%) |
| --- | --- |
| 225 | 3.3 |
| 240 | 2.0 |
| 250 | 1.7 |
| 265 | 0.4 |
| 280 | 0.3 |
| 290 | 0.3 |

The total yields of N-vinyl-N-methyl-acetamide and residual starting material are 97–98%.

The crude material from the splitting is rectified in a packed column. After distilling off the methanol which has been split off, N-vinyl-N-methylacetamide of boiling point$_{11}$ 51.5° C. is obtained in quantitative yield.

$^1$H-NMR (CDCl$_3$); 2.15 (s); 3.05 (s); 4.2–4.6 (d,d); and 6.2–6.8 (m).

EXAMPLE 2

23.4 g (0.2 mole) of N-α-methoxyethyl-N-methylformamide are flash-distilled under nitrogen in the course of 1 hour, from a 50 ml flask heated to 300° C., into a quartz tube which is 14 mm in diameter and is filled with porous silicic acid as the catalyst, 16 cm of the tube being heated to 350° C. in a tube oven. The products from the splitting are collected in a receiver which is cooled with ice. After distilling off the methanol formed, vacuum distillation of the residue gives 15 g (88% of theory) of N-vinyl-N-methyl-formamide of boiling point$_{12}$ 42°–45° C.

$^1$H-NMR (CDCl$_3$): 3.05 (d); 4.3–4.7 (m); 4.5–4.95 (dd); 7.1–7.6 (m); 8.1 (s); and 8.3 (s) ppm.

EXAMPLE 3

28.9 g (0.2 mole) of N-α-methoxyethyl-N-ethylacetamide are flash-distilled under nitrogen in the course of 1 hour, from a 50 ml flask heated to 300° C., into a quartz tube which has a diameter of 14 mm and is filled with the same catalyst as in the preceding example, 16 cm of the tube being heated to 300° C. in a tube oven. The products from the splitting are collected in a receiver which is cooled with ice.

After distilling off the methanol formed, vacuum distillation of the residue gives 20.5 g (92% of theory) of N-vinyl-N-ethyl-acetamide of boiling point$_{13}$ 62° C.

$^1$H-NMR (CDCl$_3$): 1.0–1.2 (t); 2.2 (s); 3.5–3.9 (q); 4.2–4.6 (d,d); and 6.6–8.5 (m) ppm.

EXAMPLE 4

28.9 g (0.2 mole) of N-α-ethoxyethyl-N-methylacetamide are vaporized under nitrogen in the course of 1 hour, from a 50 ml flask heated to 300° C., into a quartz tube which has a diameter of 14 mm and is filled with the same catalyst as in the preceding examples, 16 cm of the tube being heated to 300° C. in a tube oven. The products from the splitting are collected in a receiver which is cooled with ice.

After distilling off the ethanol formed, vacuum distillation of the residue gives 18 g (90% of theory) of N-vinyl-N-methyl-acetamide of boiling point$_{11}$ 51.5° C.

EXAMPLE 5

The undistilled crude product of the methylation reaction which is obtained as under Example (b) 8 is slowly distilled in a 1.20 m packed column with a reflux ratio of 1:8 under a waterpump vacuum. N-vinyl-N-methyl-acetamide is obtained as the distillate.

If the same procedure is followed using a crude methylation product which is prepared according to example (b) 7 and contains no quaternary ammonium salt, unchanged N-α-methoxyethyl-N-methyl-acetamide distils over.

(b$_1$) Splitting off of alcohol from N-α-alkoxyethyl-carboxylic acid amides

EXAMPLE 1

N-Vinylformamide

N-α-Methoxyethylformamide is flash-distilled under 100 mm Hg, with a throughput of 100 g/hour and in a weak stream of nitrogen, from a stirred flask heated to 180° C., into a quartz tube which has a diameter of 25 mm and is filled with quartz chips, 50 cm of the tube being heated. The products from the splitting are condensed in a descending condenser and collected in a receiver.

The table shows the experimental results obtained at various reaction temperatures.

The crude product is rectified via a 1.20 m Vigreux column in vacuo, with the addition of a little phenothiazine. Boiling point$_{0.2}$: 41.5° C.; n$_D^{20}$: 1.4923.

| Throughput of starting material (g/hour) | P (mm Hg) | Temperature (°C.) Vaporizer | Temperature (°C.) Reactor | Residue (%) | Yield (%) | Starting material in the crude product (mole %) |
|---|---|---|---|---|---|---|
| 100 | 100 | 180 | 510 | 3 | 94 | 7 |
| 100 | 100 | 180 | 420 | 3 | 92 | 7 |
| 100 | 100 | 180 | 350 | 3 | 88 | 18 |

EXAMPLE 2

N-Vinyl-acetamide 150 g (1.28 moles) of N-α-methoxyethylacetamide are distilled, under 190 mm Hg and in the course of 3 hours, through a glass tube which is 30 cm long and 1 cm wide and is filled with steel coils and heated to 460°–480° C. 143 g of crude product are collected in the receiver, which is cooled to −40° C. 103 g (119 moles) of crystalline N-vinylacetamide (boiling point 55° C./0.2 mm Hg), containing less than 1% of starting substance, are obtained by distillation of the crude product under 0.2 mm Hg. This corresponds to a yield of 94% of theory.

(C$_1$) Alkylation of N-vinyl-carboxylic acid amides

EXAMPLE 1

N-Vinyl-N-methyl-formamide 56 g (0.7 mole) of 50% strength sodium hydroxide solution are added dropwise to a mixture of 35.5 g (0.5 mole) of N-vinylformamide and 78 g (0.55 mole) of methyl iodide at 20° C. in the course of 3 hours, while stirring vigorously. After a further 3 hours, the mixture is decanted and the aqueous portion is extracted with methylene chloride. After stripping off of the solvent from the organic phase and distillation of the residue in vacuo, 25 g (59% of theory) of N-vinyl-N-methyl-formamide of boiling point$_{12}$ 42°–45° with a $^1$H-NMR spectrum identical to that of the product from c Example 2, are obtained.

EXAMPLE 2

N-Vinyl-N-methylacetamide

A mixture of 42.5 g (0.5 mole) of N-vinylacetamide and 78 g (0.55 mole) of methyl iodide is added dropwise to 320 g (4 moles) of vigorously stirred 50% strength sodium hydroxide solution at 20° C. 3 hours after the dropwise addition, the mixture is decanted and the aqueous portion is extracted with toluene. After stripping off the solvent from the organic phase and distilling the residue in vacuo, 32 g (65% of theory) of N-vinyl-N-methylacetamide of boiling point$_{11}$ 51.5° C. and with a $^1$H-NMR spectrum which is identical to that of the product of c Example 1, are obtained.

We claim:

1. A process for the preparation of an N-vinyl-N-alkyl carboxylic amide of the formula

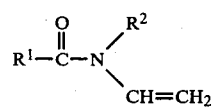

wherein R$^1$ is hydrogen, methyl or ethyl, and R$^2$ is methyl or ethyl, which comprises the steps of (a) anodically alkoxylating an N-ethyl-carboxylic acid amide of the formula

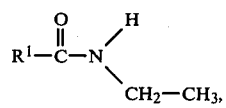

wherein R$^1$ is as defined above, with an alcohol of the formula

in which R$^3$ is alkyl of from 1 to 4 carbon atoms, in an electrolysis cell with anode material of vitreous carbon, and with at least one alkali metal alkosulfate, tetraalkylammonium alkosulfate, or mixture thereof, to produce an N-α-alkoxyethylcarboxylic acid amide of the formula

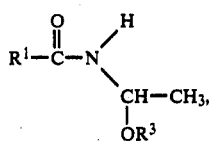

wherein $R^1$ and $R^3$ are as defined above; (b) alkylating said N-α-alkoxyethyl-carboxylic acid amide by reacting it with an alkylating agent of the formula $R^2X$, wherein $R^2$ is as defined above and X is chlorine, bromine or iodine or of the formula $R_2{}^2X$ wherein $R^2$ is as defined above and X is sulfate in an alkaline medium to give an N-α-alkoxyethyl-N-alkyl-carboxylic acid amide of the formula

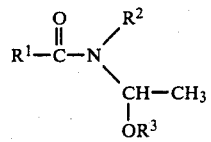

wherein $R^1$, $R^2$ and $R^3$ are as defined above; and (c) splitting off of an alcohol of the formula $R^3OH$, $R^3$ being as defined above, from said N-α-alkoxyethyl-N-alkyl-carboxylic acid amide by heating it to a temperature of from about 60° to about 350° C.; or, instead, after step (a)(b₁) splitting off an alcohol of the formula $R^3OH$, $R^3$ being as defined above, from said N-α-alkoxyethyl-carboxylic acid amide by heating to a temperature of from about 60° to about 600° C., to produce an N-vinyl carboxylic acid amide of the formula

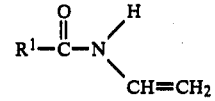

wherein $R^1$ is as defined above; and (c₁) alkylating said N-vinyl-carboxylic acid amide by reacting it in an alkaline medium with an alkylating agent of the formula $R^2X$, $R^2$ being as defined above and X being chlorine, bromine or iodine, or of the formula $R_2{}^2X$, $R^2$ being as defined above and X being sulfate.

2. A process as claimed in claim 1, wherein $R^1$ is hydrogen or methyl.

3. A process as claimed in claim 1, wherein $R^2$ is methyl.

4. A process as claimed in claim 1, wherein $R^3$ is methyl or ethyl.

5. A process as claimed in claim 4, wherein $R^3$ is methyl.

6. A process as claimed in claim 1, wherein said anodic alkoxylation is performed with tetramethylammonium sulfate.

7. A process as claimed in claim 1, wherein the alkylating agent is methyl chloride or ethyl chloride.

8. A process as claimed in claim 7, wherein the alkylating agent is methyl chloride.

9. A process as claimed in claim 1, wherein an excess of alkali and alkylating agent is maintained in the reaction mixture during the alkylation in step (b) or in step (c₁).

10. A process as claimed in claim 1, wherein the reaction of step (b) or step (c₁) is produced by sodium hydroxide or potassium hydroxide.

11. A process as claimed in claim 10, wherein said reaction is produced by sodium hydroxide.

12. A process as claimed in claim 1, wherein the alkylation in step (b) or in step (c₁) is carried out in the presence of a phase transfer catalyst.

13. A process as claimed in claim 12, wherein said alkylation is carried out in the presence of a tetraalkylammonium salt.

14. A process as claimed in claim 13, wherein said reaction is carried out in the presence of tetraalkylammonium chloride or tetraalkylammonium sulfate.

15. A process as claimed in claim 1, wherein the splitting off of alcohol in step (c) or in step (b₁) is carried out in the presence of a weakly acid catalyst.

* * * * *